United States Patent [19]

Kampf et al.

[11] 4,196,743
[45] Apr. 8, 1980

[54] FLUID TRANSFER SYSTEM

[75] Inventors: Richard S. Kampf, Costa Mesa; Richard W. Winn, Orange, both of Calif.

[73] Assignee: Beckman Instruments, Inc., Fullerton, Calif.

[21] Appl. No.: 883,080

[22] Filed: Mar. 3, 1978

[51] Int. Cl.² ............................................... G01N 1/14
[52] U.S. Cl. .................................. 137/205; 73/421 R
[58] Field of Search ...................... 137/205; 73/421 R; 141/59

[56] References Cited

U.S. PATENT DOCUMENTS

| 3,269,800 | 8/1966 | Lukrec | 141/59 X |
| 3,465,767 | 9/1969 | Peres | 137/205 X |
| 3,469,596 | 9/1969 | Branton | 137/205 |
| 3,589,197 | 6/1971 | Brooks | 73/421 R |

Primary Examiner—Alan Cohan
Attorney, Agent, or Firm—Robert J. Steinmeyer; Robert R. Meads; John R. Shewmaker

[57] ABSTRACT

A vacuum operated system for transferring fluid from a container to an open or relatively large sump without applying vacuum to the sump. A small, closed, intermediate chamber is interposed in a flow path between the container and the sump. Vacuum from a small vacuum source is applied to the intermediate chamber and draws fluid from the container through a first conduit into the chamber. A peristaltic pump draws fluid from the chamber through a second conduit to the sump while maintaining a vacuum seal for the chamber preventing loss of vacuum through the second conduit.

1 Claim, 1 Drawing Figure

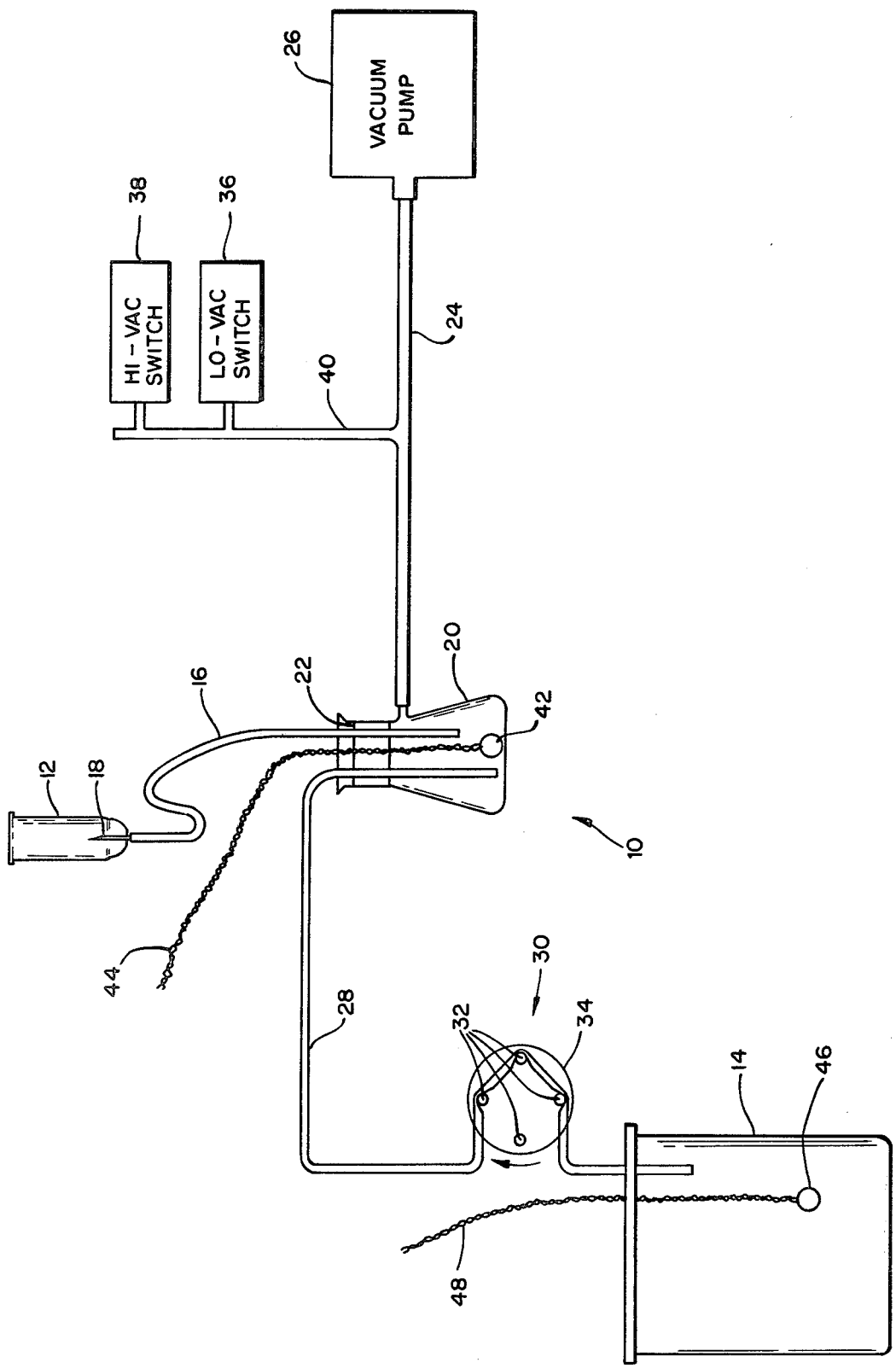

FLUID TRANSFER SYSTEM

BACKGROUND OF THE INVENTION

1. Field of the Invention

The present invention relates to vacuum operated fluid transfer systems and, more particularly, to a system for transferring fluid from a fluid container to a sump for storage, disposal, or further processing. The system is particularly useful for the vacuum withdrawal of fluid from small sample vials or reaction tubes and subsequent routing of the fluid to a sump for containment prior to disposal.

2. Description of the Prior Art

In the chemical analysis of fluids, it is often necessary to transfer fluids from one container to another. Particularly in automatic chemical analyzers, such fluid transfer is accomplished by vacuum pumping systems. Commonly such systems include a large closed receptacle having two top ports. One port is connected by a conduit to a reaction chamber containing the fluid to be transferred. The second port is connected by a conduit to a vacuum pump. When the pump is activated, a vacuum is developed within the large receptacle which draws fluid from the reaction chamber into the receptacle for storage or further processing.

While such conventional vacuum pumping systems function satisfactorily in automatic chemical analyzers, they exhibit several disadvantages. First, the large receptacle must be of sturdy and thick walled construction to withstand the vacuum applied thereto. Second, the volume of the receptacle is limited by the capacity of the vacuum pump and vice versa. That is, for a given rate of transfer of fluid from the reaction chamber to the large receptacle, an increase in volume in the receptacle must be accompanied by an increase in the capacity of the vacuum pump. If not, the rate of fluid transfer will decrease. Also, as receptacle volume increases, the time between pump activation and fluid transfer is increased since additional time is required for the pump to develop a sufficient vacuum within the receptacle to draw fluid from the reaction chamber. Finally, when the large receptacle is full, the fluid transfer system must be rendered inoperative and the vacuum and conduit connections broken for the receptacle to be emptied. This introduces a further delay in the transfer of fluids which is particularly undesirable in automated chemical analyzers. By using a smaller receptacle, the time to develop a sufficient vacuum is reduced. However, this reduction in pumping time is offset by delays resulting from the need to empty a smaller receptacle more often.

SUMMARY OF THE INVENTION

The present invention resides in an improved vacuum operated fluid transfer system which permits the transfer of fluid from a container to a sump in a manner which overcomes the disadvantages of the prior art. The system is simple and inexpensive in construction and is readily adapted for use in automatic chemical analyzers. To these ends, the fluid transfer system of the present invention comprises a fluid source, a sump, and a closed intermediate fluid chamber having an interior volume adapted to receive and contain fluid therein. First conduit means is connected between the fluid source and the intermediate chamber and second conduit means is connected between the intermediate chamber and the sump. A pneumatic line connects a vacuum source to the interior of the intermediate chamber for drawing fluid from the source through the first conduit into the chamber, such fluid being trapped by and retained within the chamber. A positive displacement pump, such as a peristaltic pump, is provided for drawing fluid out of the chamber through the second conduit toward the sump while maintaining a vacuum seal for the chamber precluding loss of vacuum therefrom through the second conduit.

With the foregoing arrangement, the sump can be an open receptacle of any desired volume or even an open sink, if desired. Since vacuum is not applied to the sump, it is unnecessary to break vacuum connections or shut down the instrument in order to empty or otherwise dispose of fluid in the sump. With a relatively small intermediate chamber, a small vacuum source is sufficient to draw fluid into the intermediate chamber. The system thus provides a simple and efficient arrangement for expeditiously transferring fluid and is thus ideally tailored for use in automated chemical analyzers in which rapid fluid delivery with minimal operator intervention and minimal instrument shutdown are desired.

BRIEF DESCRIPTION OF THE DRAWING

The FIGURE is a partial pictorial and partial schematic diagram of the fluid transfer system of the present invention.

DESCRIPTION OF THE PREFERRED EMBODIMENT

As illustrated in the drawing, the present invention is embodied in a fluid transfer system 10 comprising a fluid source or container 12, the fluid contents of which are to be removed therefrom and transferred to an open sump 14 for disposal or other disposition. While not limited thereto, the present system is adapted for use in an automated radioimmunoassay (RIA) analyzer in which a plurality of containers 12 in the form of small sample tubes or vials are provided and in each of which a reaction is conducted in solution between an antigen and a solid phase antibody. In such analysis, after the completion of the reaction, the solution is typically withdrawn from the container for disposal. The solid phase material remains in the container (trapped in a filter, for example) for subsequent measurement in a nuclear counting chamber. In the present embodiment the solution is withdrawn through a tubular conduit 16 having a hollow pointed needle 18 at one end thereof. The wall of container 12 has an area pierceable by the needle. When the container is so pierced, as illustrated, fluid therein may be withdrawn through the needle and the tubular conduit 16.

In accordance with one aspect of the invention, the fluid transfer system 10 comprises an intermediate chamber, such as a closed vacuum flask 20. The upper end of the vacuum flask is closed by a cork stopper 22 through which the end of conduit 16 remote from needle 18 passes into the interior volume of the flask. Thus arranged, the intermediate chamber is adapted to receive and contain fluid drawn from container 12 through conduit 16.

A pneumatic line 24 connects a vacuum source, illustrated as a vacuum pump 26, to the chamber of flask 20. Line 24 communicates with the flask interior near the upper end thereof so as to be displaced from the end of the conduit 16 delivering fluid to the flask. Pump 26 is actuated to apply a vacuum to the flask chamber through line 24 and hence to create a pressure differential between the chamber and the tip of needle 18. As a result, when the needle is inserted into container 12, vacuum pump 26 serves to pull fluid from the container into the flask 20. Since the connection of pneumatic line 24 to the flask is displaced above the fluid within the flask, fluid thus trapped is prevented from reaching the vacuum pump.

In accordance with a further aspect of the invention, a second tubular conduit 28 extends through stopper 22 of flask 20 and connects the flask interior to sump 14. The end of conduit 28 is positioned near the bottom of the flask so as to be immersed in any fluid therein. Significantly, a positive displacement pump 30 is disposed between the ends of conduit 28. In a preferred form, pump 30 is of the conventional peristaltic type and includes a plurality of rollers or shoulders 32 on a rotor 34 and having surfaces which engage and compress an elastomeric section of conduit 28. With the conduit thus compressed, a vacuum seal is maintained for the interior volume of flask 20 which prevents loss of vacuum from the flask through the conduit. Rotation of pump rotor 34 in a clockwise direction in the FIGURE serves to draw a series of fluid samples from the flask and to pump them to the sump. The peristaltic pump 30 may be operated continuously or intermittently, as required, to empty the flask 20.

In the foregoing arrangement, conduits 16 and 28 are flexible tubes of polytetrafluoroethylene or similar material. The elastomeric section of conduit 28 engaged by pump rollers 32 is preferably of silicone rubber.

In the RIA analyzer to which the fluid transfer system 10 has been adapted, the quantity of solution withdrawn from each reaction vial 12 is typically between two and three milliliters. Vials are presented to be drained every thirty seconds or so. Within such constraints a flask 20 having an interior volume of 250 ml has been found satisfactory. Conduits 16 and 28 have an inside diameter of 3/16". Sump 14, on the other hand, can be of any desired size. Obviously the larger the sump 14, the less frequently it needs to be emptied. If desired, the sump could simply be a sink or other receptacle or area into which the contents of flask 20 are pumped. Since vacuum is not applied to the sump, there is no need for the sump to be specifically constructed or reinforced to withstand vacuum. Moreover, since vacuum is only applied to the relatively small intermediate chamber 20, a relatively small vacuum pump having capacity to pull a vacuum of about 14-18 mm Hg has been found adequate.

Operation of the fluid transfer system is monitored by several detectors and associated switches which respond to predetermined operating conditions. The pressure in pneumatic line 24 is monitored by two vacuum switches 36 and 38 tapped into line 24 through a conduit stub 40. The vacuum switches are of conventional design incorporating a diaphragm or similar structure exposed to the vacuum and which actuates a pair of switch contacts when the vacuum exceeds a predetermined threshold value. Each switch thus provides an indication of whether the vacuum is above or below the threshold value. For this purpose, each switch is connected to a suitable indicator or control unit (not shown) responsive to operation of the switches for indicating the vacuum condition or automatically effecting control functions in response thereto. In this respect, the pressure threshold of switch 36 is set at a minimum level necessary to withdraw fluid from vial 12. Needle 18 is not inserted into the vial unless switch 36 indicates that the vacuum in line 24 is above this minimum level. The pressure threshold of switch 38 is set at a higher value which should be attained after the needle is inserted into the vial. Switch 38 thus indicates whether the needle successfully penetrates the vial. Moreover, after the needle is withdrawn from the vial, the vacuum should drop below the threshold of switch 38. If the pressure does not drop at this time, it is an indication that conduit 16 is probably clogged. In the present system the pressure thresholds of switches 36 and 38 are set at fourteen and eighteen mm Hg, respectively.

A conventional, eccentrically weighted float switch 42 is disposed in flask 20 to signal an overflow condition in the flask and hence a probable malfunction of peristaltic pump 30. The float switch includes a pair of conductors 44 extending through and sealed in cork 22. Consequently, when the fluid reaches a level in the chamber sufficient to float the switch, the switch flips over closing internal contacts and signaling an overflow condition. A similar float switch 46 and conductors 48 are suspended within sump 14 to signal a fluid level requiring that the sump be emptied. Both float switches are coupled to a suitable indicator or control unit (not shown) responsive to operation of the switches for signaling an overflow condition, inhibiting system operation, or the like.

In operation, upon completion of a reaction in container 12, needle 18 is driven through the pierceable wall area of the container. Fluid is drawn by vacuum from the container through conduit 16 into the chamber of flask 20. Fluid thus trapped within the flask is pumped through conduit 28 to sump 14 by peristaltic pump 30. The operation is repeated in succession for each container to be drained. It is thus seen that the fluid transfer system of the invention provides an extremely simple and inexpensive arrangement for rapidly transferring fluid from a source or container 12 to a sump 14 without the complexities and operational difficulties of the prior art. The system functions continuously with minimal operator intervention. It is unnecessary to break the vacuum system to empty the sump. Consequently, there is no shutdown of the system or other delay to dispose of the fluid. Sump 14 can be emptied even while the system is operating with the flask 20 collecting fluids until sump 14 is replaced or returned. The system thus is particularly advantageous for use in automated chemical analyzers requiring rapid and expeditious fluid transfer from a series of containers without system interruption or shutdown or other operational delays. Moreover, while a preferred embodiment of the invention has been illustrated and described, various modifications may be made therein without departing from the invention as defined by the appended claims.

What is claimed is:

1. A fluid transfer system for transferring fluid from a fluid source to a sump for disposal or other disposition comprising;

a single closed intermediate fluid chamber having an interior volume adapted to receive and contain fluid therein;

first fluid conduit means connected between the fluid source and the chamber for delivering fluid to the chamber;

a vacuum source;

a pneumatic line connecting the vacuum source directly to the interior of the chamber and for applying a vacuum thereto sufficient to draw fluid from the source through the first conduit means into the chamber, the connection of the pneumatic line to the chamber being at a location displaced from an end of the first fluid conduit delivering fluid to the chamber such that the chamber serves as a trap for such fluid preventing same from reaching the vacuum source;

second fluid conduit means connected between the chamber and the sump and having one end immersed in fluid within the chamber and further including an elastomeric tubular portion; and positive displacement pump means for drawing fluid from the chamber against the vacuum applied thereto through the second conduit means and for positively driving fluid to the sump while maintaining a vacuum seal between the chamber and the sump to prevent loss of vacuum through the second conduit means, the pump means being of the peristaltic type having one or more rotor surfaces for compressively engaging the tubular portion of the second conduit to establish the vacuum seal and for moving therealong to pump fluid through the second conduit means to the sump.

* * * * *